United States Patent
Augier et al.

(10) Patent No.: US 10,857,514 B2
(45) Date of Patent: Dec. 8, 2020

(54) PROCESS FOR THE OLIGOMERIZATION OF ETHYLENE WITH STIRRED GAS/LIQUID REACTOR AND PLUG-FLOW REACTOR SEQUENCE

(71) Applicant: IFP Energies nouvelles, Rueil-Malmaison (FR)

(72) Inventors: Frederic Augier, Rueil-Malmaison (FR); Alexandre Vonner, Rueil-Malmaison (FR); Tiago Sozinho, Rueil-Malmaison (FR); Natacha Touchais, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/456,313

(22) Filed: Jun. 28, 2019

(65) Prior Publication Data
US 2020/0001266 A1   Jan. 2, 2020

(30) Foreign Application Priority Data
Jun. 28, 2018   (FR) ..................... 18 55866

(51) Int. Cl.
| | |
|---|---|
| B01J 19/24 | (2006.01) |
| B01F 3/04 | (2006.01) |
| B01J 8/18 | (2006.01) |
| B01J 8/22 | (2006.01) |
| B01J 23/26 | (2006.01) |

(Continued)

(52) U.S. Cl.
CPC ......... *B01J 19/248* (2013.01); *B01F 3/04106* (2013.01); *B01J 8/1818* (2013.01); *B01J 8/22* (2013.01); *B01J 23/26* (2013.01); *B01J 23/755* (2013.01); *C07C 2/24* (2013.01); *B01J 2231/20* (2013.01); *C07C 11/08* (2013.01);

(Continued)

(58) Field of Classification Search
CPC ........ B01J 19/248; B01J 23/755; B01J 23/26; B01J 8/22; B01J 8/1818; B01J 2231/20; B01J 23/00; B01J 19/245; B01J 19/2415; B01J 19/002; B01J 19/0013; B01J 2219/185; B01J 2219/00254; B01J 2219/00087; C07C 2/24; C07C 2523/755; C07C 2523/26; C07C 2521/06; C07C 11/107; C07C 11/08; B01F 3/04106; C10G 50/00

USPC ........................................ 422/131
See application file for complete search history.

(56) References Cited

U.S. PATENT DOCUMENTS 3,691,095 A * 9/1972 Kroll ................. B01J 31/143
                                                  502/102
5,013,801 A   5/1991 Cozewith et al.
(Continued)

FOREIGN PATENT DOCUMENTS

| EP | 0780353 B1 | 8/2000 |
| FR | 2959736 A1 | 11/2011 |
| WO | 05019280 A1 | 3/2005 |

OTHER PUBLICATIONS

Office Action in FR1855866 dated Jan. 11, 2019 (pp. 1-4).

*Primary Examiner* — Huy Tram Nguyen
(74) *Attorney, Agent, or Firm* — Millen White Zelano and Branigan, PC; John Sopp

(57) ABSTRACT

Reaction device which makes possible the oligomerization of olefins to give linear olefins and preferably linear α-ole- (Continued)

fins, comprising a gas/liquid reactor and a reactor of plug-flow type. The reaction device is also employed in an oligomerization process.

24 Claims, 3 Drawing Sheets

(51) Int. Cl.
  *B01J 23/755* (2006.01)
  *C07C 2/24* (2006.01)
  *C07C 11/08* (2006.01)
  *C07C 11/107* (2006.01)

(52) U.S. Cl.
  CPC ........ *C07C 11/107* (2013.01); *C07C 2521/06* (2013.01); *C07C 2523/26* (2013.01); *C07C 2523/755* (2013.01)

(56) References Cited

U.S. PATENT DOCUMENTS

| | | | |
|---|---|---|---|
| 5,856,612 | A | 1/1999 | Araki et al. |
| 5,859,303 | A | 1/1999 | Lashier |
| 7,514,508 | B2 | 4/2009 | Meier et al. |
| 8,618,342 | B2 | 12/2013 | Guillon et al. |
| 9,586,831 | B2* | 3/2017 | Fujita ................ B01J 12/00 |
| 2005/0187418 | A1 | 8/2005 | Small et al. |
| 2006/0171868 | A1* | 8/2006 | Filippi ................ B01J 8/0492 |
| | | | 422/600 |
| 2016/0229766 | A1* | 8/2016 | Sydora ................ B01J 31/143 |
| 2017/0081257 | A1* | 3/2017 | Kreischer ................ B01J 4/02 |

\* cited by examiner

Curve A (♦)

Curve B (X)

PROCESS FOR THE OLIGOMERIZATION OF ETHYLENE WITH STIRRED GAS/LIQUID REACTOR AND PLUG-FLOW REACTOR SEQUENCE

TECHNICAL FIELD

The present invention relates to a process for the oligomerization of olefins to give linear olefins, and preferably linear α-olefins, employing a specific reaction device. The process relates in particular to the oligomerization of ethylene to give linear α-olefins, such as but-1-ene, hex-1-ene or oct-1-ene, or a mixture of linear α-olefins.

PRIOR ART

The invention relates to the field of processes for the oligomerization, in particular for the dimerization, trimerization or tetramerization, of olefins to give linear olefins and more particularly to give linear α-olefins. The present invention applies to all the processes for the oligomerization of olefins, such as, for example, the trimerization of ethylene to give hex-1-ene, presented in the continuation of the description.

Typically, oligomerization processes are carried out in gas/liquid reactors, also known as bubble point reactors. Due to the exothermic nature of oligomerization reactions, bubble point reactors also comprise a loop for recirculation of a liquid fraction. The good heat transfer capacity related to the recirculation loop makes it possible to obtain a good homogeneity of the concentrations and to control the temperature throughout the reaction volume.

For a given operating temperature and a given operating pressure, the performance qualities of such a bubble reactor, in terms of selectivity and of conversion, are limited by the kinetic scheme inherent to the catalytic system (the main and secondary reactions) and to the operating conditions under consideration (the temperature and the pressure).

The main oligomerization reactions correspond to the reactions for the dimerization, trimerization and tetramerization of the starting olefins to give final linear olefins, for example the conversion of ethylene to give hex-1-ene. The secondary reactions correspond to the reactions of the final linear olefins obtained during the main reactions, such as, for example, the reaction of hex-1-ene with ethylene to produce decenes. These secondary reactions result in a decrease in the yield of linear olefins in favour of non-upgradable byproducts.

These byproducts associated with the operating conditions create a performance ceiling such as represented in the curve for selectivity as a function of the conversion (see FIG. 2A, described here in the case of the selective trimerization of ethylene to give hex-1-ene).

In particular, the processes of the prior art, employing a bubble point reactor, as illustrated in FIG. 1, do not make it possible to simultaneously achieve high levels of selectivity for linear olefins, more particularly for linear α-olefins, and high levels of conversion.

Surprisingly, the Applicant Company has discovered a specific implementation of the oligomerization process which makes it possible to simultaneously achieve higher levels of selectivity and of conversion than in the prior art. The process employs a gas/liquid reactor and a plug-flow reactor and also a recirculation loop comprising a heat exchanger. Advantageously, the control of the temperature in the said plug-flow reactor makes it possible to earn conversion points, with an unchanging selectivity, this being the case despite the exothermicity of the reaction. Thus, the plug-flow reactor makes it possible to obtain an increase in the conversion, while retaining a virtually constant selectivity for linear olefins and in particular for α-olefins. These advantages make it possible to limit the costs for implementation of the said process.

SUBJECT-MATTER OF THE INVENTION

The Applicant Company has developed a device comprising:
- a gas/liquid reactor 1, of elongated shape along the vertical axis, comprising a liquid phase and a gas phase located above the said liquid phase,
- a means for introduction of the olefin 3 into the gas/liquid reactor employing a means for injection of the olefin within the said liquid phase of the gas/liquid reactor,
- a means for introduction of the catalytic system 14 into the gas/liquid reactor,
- a recirculation loop 13 comprising withdrawal means in the gas/liquid reactor for the withdrawal and the dispatch of a fraction of withdrawn liquid to a heat exchanger capable of cooling the said liquid fraction, and means for introduction of the said cooled liquid, exiting from the heat exchanger, into the upper part of the gas/liquid reactor 1,
- a reactor of plug-flow type 11 comprising withdrawal means in the gas/liquid reactor for the withdrawal and the dispatch of a fraction of withdrawn liquid to the plug-flow reactor and means for recovery of a reaction effluent, at the outlet of the plug-flow reactor.

The Applicant Company has also discovered that the said device can be employed in an olefin oligomerization process at a pressure between 1.0 and 10.0 MPa and at a temperature between 0 and 200° C., comprising the following stages:
a) a catalytic oligomerization system comprising at least one metal precursor and at least one activating agent is introduced into a gas/liquid reactor 1 comprising a liquid phase and a gas phase;
b) the said catalytic system is brought into contact with the olefin by introducing the said olefin 3 into the gas/liquid reactor 1;
c) the reaction liquid is withdrawn 4 in the lower part of the said gas/liquid reactor;
d) a first fraction of the liquid 9 withdrawn in stage c) is sent to a heat exchanger 2 in order to obtain a cooled liquid fraction and then the said cooled liquid fraction is reintroduced into the upper part of the said gas/liquid reactor;
e) a second fraction of the liquid 10 withdrawn in stage c) is sent to a reactor of plug-flow type 11, the residence time of the said liquid fraction in the reactor of plug-flow type being between 1 and 30 minutes, the increase in temperature of the said fraction in the reactor of plug-flow type being limited to between 1.0 and 11.0° C.;
f) a reaction effluent 6 is recovered at the outlet of the reactor of plug-flow type.

Definitions & Abbreviations

The following terms are defined in order to improve the understanding of the invention:

The term "oligomerization" denotes any addition reaction of a first olefin with a second olefin identical to or different from the first olefin and comprises dimerization, trimerization and tetramerization. The olefin thus obtained is of $C_nH_{2n}$ type, where n is equal to or greater than 4.

The term "olefin" denotes both an olefin and a mixture of olefins.

The term "α-olefin" denotes an olefin in which the double bond is located at the terminal position of the alkyl chain.

The term "heteroatom" is an atom other than carbon and hydrogen. A heteroatom can be chosen from oxygen, sulfur, nitrogen, phosphorus, silicon and halides, such as fluorine, chlorine, bromine or iodine.

The term "hydrocarbon" is an organic compound consisting exclusively of carbon (C) and hydrogen (H) atoms of empirical formula $C_mH_p$, with m and p natural integers.

The term "catalytic system" denotes a mixture of at least one metal precursor, of at least one activating agent, optionally of at least one additive and optionally of at least one solvent.

The term "alkyl" is a saturated or unsaturated, linear or branched, non-cyclic, cyclic or polycyclic hydrocarbon chain comprising between 1 and 20 carbon atoms, preferably from 2 to 15 carbon atoms and more preferably still from 2 to 8 carbon atoms, denoted $C_1$-$C_{20}$ alkyl. For example, $C_1$-$C_6$ alkyl is understood to mean an alkyl chosen from the methyl, ethyl, propyl, butyl, pentyl, cyclopentyl, hexyl and cyclohexyl groups.

The term "aryl" is a fused or non-fused, mono- or polycyclic, aromatic group comprising between 6 and 30 carbon atoms, denoted $C_6$-$C_{30}$ aryl.

The term "alkoxy" is a monovalent radical consisting of an alkyl group bonded to an oxygen atom, such as the $C_4H_9O$— group.

The term "aryloxy" is a monovalent radical consisting of an aryl group bonded to an oxygen atom, such as the $C_6H_5O$— group.

The term "liquid phase" denotes the mixture of all the compounds which occur in the liquid physical state under the temperature and pressure conditions of the gas/liquid reactor.

The term "gas phase" denotes the mixture of all the compounds which occur in the gas physical state under the temperature and pressure conditions of the gas/liquid reactor: in the form of bubbles present in the liquid, and also in the top part of the gas/liquid reactor (also known as headspace of the reactor).

The term "lower part" of the gas/liquid reactor denotes the lower half of the reactor.

The term "upper part" of the gas/liquid reactor denotes the upper half of the reactor.

The term "reactor of plug-flow type" or "plug-flow reactor" denotes a reactor with a flow of plug-flow type.

The term "withdrawal flow rate" denotes the weight of liquid withdrawn from the reactor per unit of time; it is expressed in tonnes per hour (t/h).

The term "non-condensable gas" denotes a byproduct resulting from the side reactions, in the gas physical form under the temperature and pressure conditions of the process, which accumulates in the headspace of the reactor. The non-condensable gases are, for example, ethane, methane or butane (non-exhaustive list).

The term "cocurrent" denotes the circulation of a first fluid in the same direction of circulation as a second fluid.

The term "contact surface area" represents the surface area where heat exchanges take place between the liquid fraction present in the plug-flow reactor and the cooling liquid.

The term "solvent" denotes a liquid which has the property of dissolving, diluting or extracting other substances without chemically modifying them and without itself being modified.

The expression "between . . . and . . . " should be understood as including the limits mentioned.

BRIEF DESCRIPTION OF THE FIGURES

The present invention is not limited to the implementations represented in the figures. The subject-matter of the invention is illustrated in the figures through the specific case of the trimerization of ethylene to give hex-1-ene.

The figures do not represent all of the means necessary for the implementation of the devices known to a person skilled in the art, such as the means for injection of the catalytic system, of the olefin, optionally of a solvent, the gas distributor, nor the means for control of the pressure and the temperature of the plug-flow and gas/liquid reactors. The subject-matter of the present invention is not limited to the specific case of the trimerization of hex-1-ene, illustrated in the continuation of the description.

FIG. 2A is a diagram representing the selectivity for hex-1-ene as a function of the conversion of ethylene in a trimerization process according to the prior art (represented by points), comprising a standard gas/liquid reactor. The profile of the curve of FIG. 2A is substantially similar for all of the oligomerization reactions of olefins. It is important to note the difficulty in obtaining both a high level of conversion of ethylene (as % of ethylene converted) and a high selectivity for desired linear olefin(s) (as % by weight of the reaction products).

FIG. 2B is a diagram representing the selectivity for hex-1-ene as a function of the conversion of ethylene in a trimerization process according to the invention (represented by crosses), comprising a gas/liquid reactor, a plug-flow reactor and a recirculation loop comprising a heat exchanger. The profile of the curve of FIG. 2B, obtained by the process according to the invention for the trimerization reaction of ethylene to give hex-1-ene, is representative of the technical effect of the invention, which is not limited to the trimerization. This is because this effect can be obtained for all oligomerization reactions of olefins and in particular dimerization and tetramerization reactions of ethylene.

DETAILED DESCRIPTION OF THE INVENTION

Figure 1:
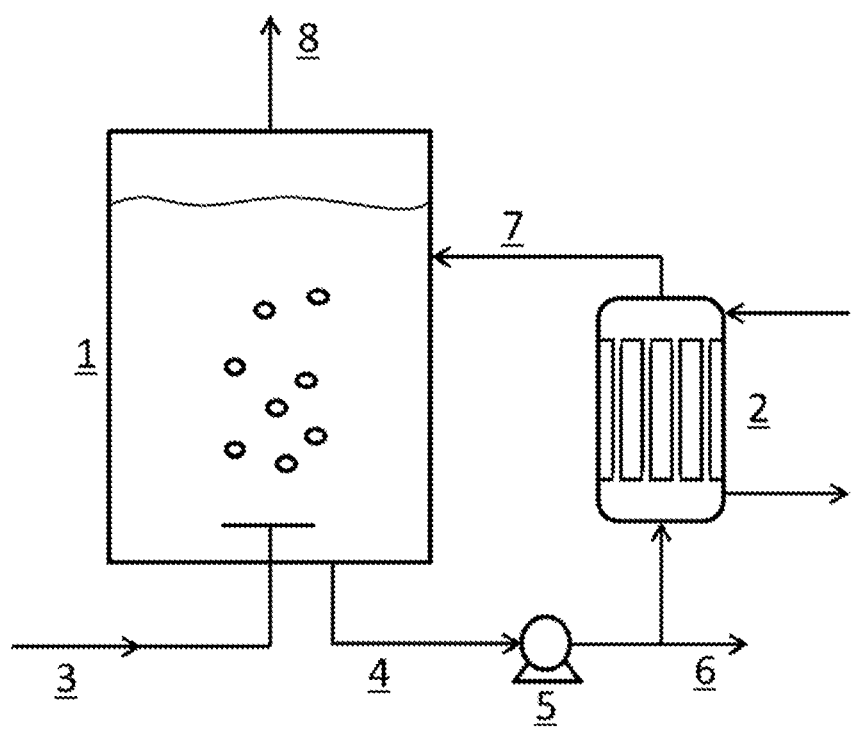
FIG. 1 illustrates a reaction device according to the prior art, consisting of a single gas/liquid reactor of bubble column type, with introduction of olefin via introduction means 3. Withdrawal means 4 make it possible, by virtue of a liquid recirculation pump 5, to send a fraction of withdrawn liquid to a heat exchanger 2 which makes it possible to remove the heat produced by the reaction and to feed, with cooled liquid, the top of the gas/liquid reactor via means for introduction of the cooled liquid 7. The gas/liquid reactor comprises means for bleeding off 8 the non-condensable gases in the gas headspace, at the top of the reactor. The effluent from the oligomerization process is recovered via the line 6.

Within the meaning of the present invention, the different embodiments presented can be used alone or in combination with one another, without any limit to the combinations.

In the continuation of the description, the subject-matter of the invention is illustrated in particular through the case of the trimerization of ethylene to give hex-1-ene.

The Applicant Company has discovered that it is possible to improve the conversion, while retaining a high selectivity for desired linear olefin(s), and in particular α-olefin(s), by providing an oligomerization process comprising a sequence of a gas/liquid reactor of bubble column type and of a reactor of plug-flow type. The reactor of plug-flow type makes it possible to gain in conversion with a selectivity at a given value, as a result of the plug flow and of the limitation on the increase in temperature, making it possible for the conversion of the olefins to continue in the reactor of plug-flow type.

The invention thus relates to a device comprising:
- a gas/liquid reactor 1, of elongated shape along the vertical axis, comprising a liquid phase and a gas phase located above the said liquid phase,
- a means for introduction of the olefin 3 into the gas/liquid reactor employing a means for injection of the olefin within the said liquid phase of the gas/liquid reactor,
- a means for introduction of the catalytic system 14 into the gas/liquid reactor,
- a recirculation loop 13 comprising withdrawal means in the gas/liquid reactor for the withdrawal and the dispatch of a fraction of withdrawn liquid to a heat exchanger capable of cooling the said liquid fraction, and means for introduction of the said cooled liquid, exiting from the heat exchanger, into the upper part of the gas/liquid reactor 1,
- a reactor of plug-flow type 11 comprising withdrawal means in the gas/liquid reactor for the withdrawal and the dispatch of a fraction of withdrawn liquid to the plug-flow reactor and means for recovery of a reaction effluent, at the outlet of the plug-flow reactor.

The invention also relates to an olefin oligomerization process employing the device, at a pressure between 1.0 and 10.0 MPa and at a temperature between 0° C. and 200° C., comprising the following stages:
a) a catalytic oligomerization system comprising at least one metal precursor and at least one activating agent is introduced into a gas/liquid reactor 1 comprising a liquid phase and a gas phase;
b) the said catalytic system is brought into contact with the olefin by introducing the said olefin 3 into the gas/liquid reactor 1;
c) the reaction liquid is withdrawn 4 in the lower part of the said gas/liquid reactor;
d) a first fraction of the liquid 9 withdrawn in stage c) is sent to a heat exchanger 2 in order to obtain a cooled liquid fraction and then the said cooled liquid fraction is reintroduced into the upper part of the said gas/liquid reactor;
e) a second fraction of the liquid 10 withdrawn in stage c) is sent to a reactor of plug-flow type 11, the residence time of the said liquid fraction in the reactor of plug-flow type being between 1 and 30 minutes, the increase in temperature of the said fraction in the reactor of plug-flow type being limited to between 1.0 and 11.0° C.;
f) a reaction effluent 6 is recovered at the outlet of the reactor of plug-flow type.

Oligomerization Process

The process according to the invention makes it possible to obtain linear olefins and in particular linear α-olefins by bringing olefin(s) and a catalytic system into contact, optionally in the presence of an additive and optionally in the presence of a solvent, and by the use of a gas/liquid reactor, a plug-flow reactor and a recirculation loop comprising a heat exchanger.

The oligomerization process is carried out at a pressure between 1.0 and 10.0 MPa, preferably between 2.0 and 8.0 MPa, more preferably between 4.0 and 8.0 MPa and more particularly between 6.0 and 8.0 MPa. The temperature is between 0° C. and 200° C., preferably between 30° C. and 180° C., more preferably between 30° C. and 150° C. and more preferably still between 40° C. and 140° C.

Stage a) of Introduction of the Catalytic System

The process according to the invention comprises a stage a) of introduction of the catalytic system into a gas/liquid reactor comprising a liquid phase and a gas phase. The introduction of the catalytic system can be carried out both in the lower part of the reactor and in the recirculation loop; preferably, the introduction of the catalytic system is carried out in the recirculation loop.

Any catalytic system known to a person skilled in the art and capable of being employed in the dimerization, trimerization or tetramerization processes and more generally in the oligomerization processes according to the invention comes within the field of the invention. The said catalytic systems and also their implementations are described in particular in Applications FR 2 984 311, FR 2 552 079, FR 3 019 064, FR 3 023 183, FR 3 042 989 or also in Application FR 3 045 414.

Preferably, the catalytic systems comprise, preferably consist of:
- a metal precursor, preferably based on nickel, on titanium or on chromium,
- an activating agent,
- optionally an additive, and
- optionally a solvent.

The Metal Precursor

The metal precursor used in the catalytic system is chosen from compounds based on nickel, on titanium or on chromium.

In one embodiment, the metal precursor is based on nickel and preferably comprises nickel with a (+II) oxidation state. Preferably, the nickel precursor is chosen from nickel(II) carboxylates, such as, for example, nickel 2-ethylhexanoate, nickel(II) phenates, nickel(II) naphthenates, nickel(II) acetate, nickel(II) trifluoroacetate, nickel(II) triflate, nickel(II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferably comprises a titanium aryloxy or alkoxy compound.

The titanium alkoxy compound advantageously corresponds to the general formula $[Ti(OR)_4]$ in which R is a linear or branched alkyl radical. Mention may be made, among the preferred alkoxy radicals, as nonlimiting example, of tetraethoxy, tetraisopropoxy, tetra(n-butoxy) and tetra(2-ethylhexyloxy).

The titanium aryloxy compound advantageously corresponds to the general formula $[Ti(OR')_4]$ in which R' is an aryl radical substituted or unsubstituted by alkyl or aryl groups. The R' radical can comprise heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy, biphenoxy, binaphthoxy or 1,8-naphthalenedioxy.

According to a third embodiment, the metal precursor is based on chromium and preferably comprises a chromium (II) salt, a chromium(III) salt or a salt with a different oxidation state which can comprise one or more identical or different anions, such as, for example, halides, carboxylates, acetylacetonates or alkoxy or aryloxy anions. Preferably, the chromium-based precursor is chosen from $CrCl_3$, $CrCl_3(tetrahydrofuran)_3$, $Cr(acetylacetonate)_3$, $Cr(naphthenate)_3$, $Cr(2-ethylhexanoate)_3$ or $Cr(acetate)_3$.

The concentration of nickel, of titanium or of chromium is between 0.01 and 300.0 ppm by weight of atomic metal, with respect to the reaction mass, preferably between 0.02 and 100.0 ppm, preferably between 0.03 and 50.0 ppm, more preferably between 0.5 and 20.0 ppm and more preferably still between 2.0 and 50.0 ppm by weight of atomic metal, with respect to the reaction mass.

The Activating Agent

Whatever the metal precursor, the catalytic system additionally comprises one or more activating agents chosen from aluminium-based compounds, such as methylaluminium dichloride ($MeAlCl_2$), dichloroethylaluminium ($EtAlCl_2$), ethylaluminium sesquichloride ($Et_3Al_2Cl_3$), chlorodiethylaluminium ($Et_2AlCl$), chlorodiisobutylaluminium ($i-Bu_2AlCl$), triethylaluminium ($AlEt_3$), tripropylaluminium ($Al(n-Pr)_3$), triisobutylaluminium ($Al(i-Bu)_3$), diethylethoxyaluminium ($Et_2AlOEt$), methylaluminoxane (MAO), ethylaluminoxane and modified methylaluminoxanes (MMAO).

The Additive

Optionally, the catalytic system comprises one or more additives.

When the catalytic system is based on nickel, the additive is chosen from:
compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or compounds of phosphine type independently chosen from tributylphosphine, triisopropylphosphine, tricyclopentylphosphine, tricyclohexylphosphine, triphenylphosphine, tris(o-tolyl)phosphine, bis(diphenylphosphino)ethane, trioctylphosphine oxide, triphenylphosphine oxide or triphenyl phosphite, or the compounds corresponding to the general formula (I) or one of the tautomers of the said compound:

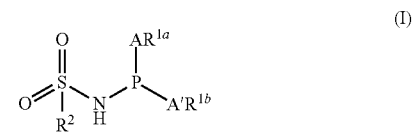

in which:

A and A', which are identical or different, are independently an oxygen or a single bond between the phosphorus atom and a carbon atom, the $R^{1a}$ and $R^{1b}$ groups are independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-di(trifluoromethyl)phenyl, benzyl, naphthyl, bisnaphthyl, pyridyl, bisphenyl, furanyl or thiophenyl groups, the $R^2$ group is independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl or thiophenyl groups.

When the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-di(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl) ether, benzofuran, glyme and diglyme, taken alone or as a mixture.

When the catalytic system is based on chromium, the additive is chosen from:

the aryloxy compounds of general formula $[M(R^3O)_{2-n}X_n]_y$, in which:

M is chosen from magnesium, calcium, strontium and barium, preferably magnesium, $R^3$ is an aryl radical containing from 6 to 30 carbon atoms and X is a halogen or an alkyl radical containing from 1 to 20 carbon atoms, n is an integer which can take the values of 0 or 1, and y is an integer of between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals can be carried by one and the same molecule, such as, for example, biphenoxy, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy.

The Solvent

In another embodiment according to the invention, the catalytic system optionally comprises one or more solvents.

The solvent is chosen from the group formed by aliphatic and cycloaliphatic hydrocarbons, such as hexane, cyclohexane, heptane, butane or isobutane.

Preferably, the solvent used is cyclohexane.

Stage b) of Bringing into Contact with the Olefin

The process according to the invention comprises a stage b) in which the catalytic system is brought into contact with the olefin or the mixture of olefins. Preferably, the olefin is ethylene.

Preferably, the olefin is introduced by dispersion in the liquid phase of the gas/liquid reactor, preferentially in the lower part of the gas/liquid reactor, by a means capable of producing the said dispersion in a uniform manner over the entire section of the reactor. Preferably, the dispersion means is chosen from a distributing system with a homogeneous distribution of the points for introduction of the olefin over the entire section of the reactor.

The olefin is introduced by at least one means for admission under the control of the pressure, which keeps the latter constant in the reactor. The admission means is any means well known to a person skilled in the art, such as a valve.

Preferably, the olefin is introduced at a flow rate of between 1 and 200 t/h, preferably between 3 and 150 t/h, preferably between 5 and 100 t/h and preferably between 5 and 50 t/h.

According to a specific embodiment of the invention, a stream of gaseous hydrogen can also be introduced into the gas/liquid reactor, with a flow rate representing from 0.2% to 1.0% by weight of the flow rate of olefin introduced. Preferably, the stream of gaseous hydrogen is introduced by the means employed for the introduction of the olefin.

According to one embodiment, the catalytic oligomerization reaction is carried out continuously and in homogeneous catalysis, in the absence of support. The introduction of the olefin can be carried out just as easily via the means for introduction of the catalytic system, that is to say in the recirculation loop or in the lower part of the reactor, as independently.

Stage c) of Withdrawal of the Reaction Liquid

The process according to the invention comprises a stage c) of withdrawal of the reaction liquid. The withdrawal is carried out from a point located in the lower part of the gas/liquid reactor, preferably under the level of introduction of the olefin and preferably in the bottom of the reactor. The withdrawal is carried out by any means capable of carrying out the withdrawal and preferably by using a pump.

The reaction mixture of the gas/liquid reactor is withdrawn via an admission means under the control of the liquid level, so as to keep the latter constant. The admission means is any means well known to a person skilled in the art, such as a valve.

Preferably, the withdrawal flow rate is between 500 and 12 000 t/h and preferably between 800 and 8500 t/h. The withdrawal flow rate is regulated in order to maintain a constant liquid level in the gas/liquid reactor.

Figure 3:
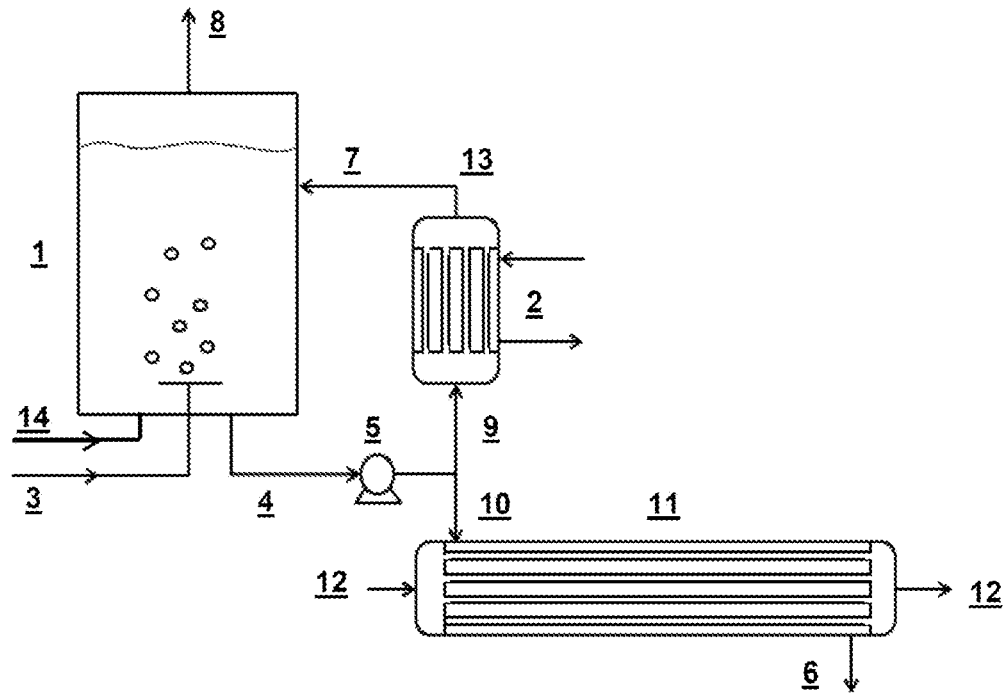
FIG. 3 illustrates a device which makes possible the implementation of the process according to the invention, comprising a gas/liquid reactor 1 of bubble column type, means for introduction of the catalytic system 14, means for introduction olefins 3, a recirculation loop 13 which makes possible the passage of a portion of the withdrawn liquid fraction 9 into a heat exchanger 2 and then the reintroduction of the said fraction into the reactor, and a reactor of plug-flow type 11 fed with a second fraction of withdrawn liquid 10, making possible the extraction of the reaction effluent.

The withdrawal can be carried out at a point of the gas/liquid reactor (as represented in FIG. 3) in order to feed with liquid phase, via one and the same withdrawal line 4, the recirculation loop of stage d) and the reactor of plug-flow type used in stage e) of the process according to the invention.

According to an alternative embodiment (not represented in the figures), several withdrawal points can be present in the gas/liquid reactor: a first point making possible the withdrawal of the reaction liquid intended for the recirculation loop of stage d) and a second point for withdrawal of the reaction liquid intended for stage e).

Stage d) of Dispatch of the Liquid Fraction to a Recirculation Loop

The process according to the invention comprises a stage d) in which a first fraction of the reaction liquid withdrawn in stage c) is sent to a heat exchanger in order to obtain a cooled liquid fraction and then the said cooled liquid fraction is reintroduced into the upper part of the gas/liquid reactor.

Preferably, the said stage consisting in cooling the first liquid fraction is carried out by the circulation of a first fraction of the withdrawn reaction liquid through one or more heat exchangers located inside or outside the reactor, and preferably outside.

As the reaction is exothermic, it is necessary to remove the heat produced by the reaction by cooling the liquid from the gas/liquid reactor in order to control the temperature in the whole of the reactor and thus to make possible the progression of the reaction.

The heat exchanger advantageously makes it possible to reduce the temperature of the said first part by 1.0 to 11.0° C., preferably by 2.0 to 10.0° C., preferably by 3.0 to 9.0° C. Advantageously, the cooling of the said first part makes it possible to keep the temperature of the reaction medium within the desired temperature ranges. Any type of heat exchanger known to a person skilled in the art which makes it possible to carry out the said process can be used.

The cooled liquid fraction is subsequently reintroduced into the upper part of the gas/liquid reactor, preferably at the top of the said reactor, in a preferred way into the gas phase, by any means known to a person skilled in the art. Preferably, the flow rate for introduction of the said first cooled part is between 500 and 12 000 t/h and preferably between 800 and 8500 t/h.

Advantageously, carrying out the cooling of the first liquid fraction via the recirculation loop also makes it possible to carry out the stirring of the medium and thus to homogenize the concentrations of the reactive entities throughout the liquid volume of the reactor.

Stage e) of Dispatch of the Liquid Fraction to a Plug-Flow Reactor

The process according to the invention comprises a stage e) in which a second fraction of the liquid withdrawn in stage c) is sent to a plug-flow reactor.

The flow rate for introduction of the said liquid fraction into the reactor of plug-flow type is between 500 and 12 000 t/h and preferably between 800 and 8500 t/h. Preferably, the flow rate for withdrawal of the liquid fraction intended for stage e) is from 5 to 200 times lower than the flow rate for withdrawal of the liquid fraction intended for stage d). Very preferably, the flow rate for withdrawal of the liquid fraction intended for stage e) is from 5 to 150 times lower, preferably from 10 to 120 times lower and in a preferred way from 20 to 100 times lower than the flow rate for withdrawal of the liquid fraction intended for stage d).

The residence time of the said liquid fraction in the plug-flow reactor is between 1 and 30 minutes, preferably between 5 and 20 minutes and more preferably still between 5 and 15 minutes.

Figure 4:
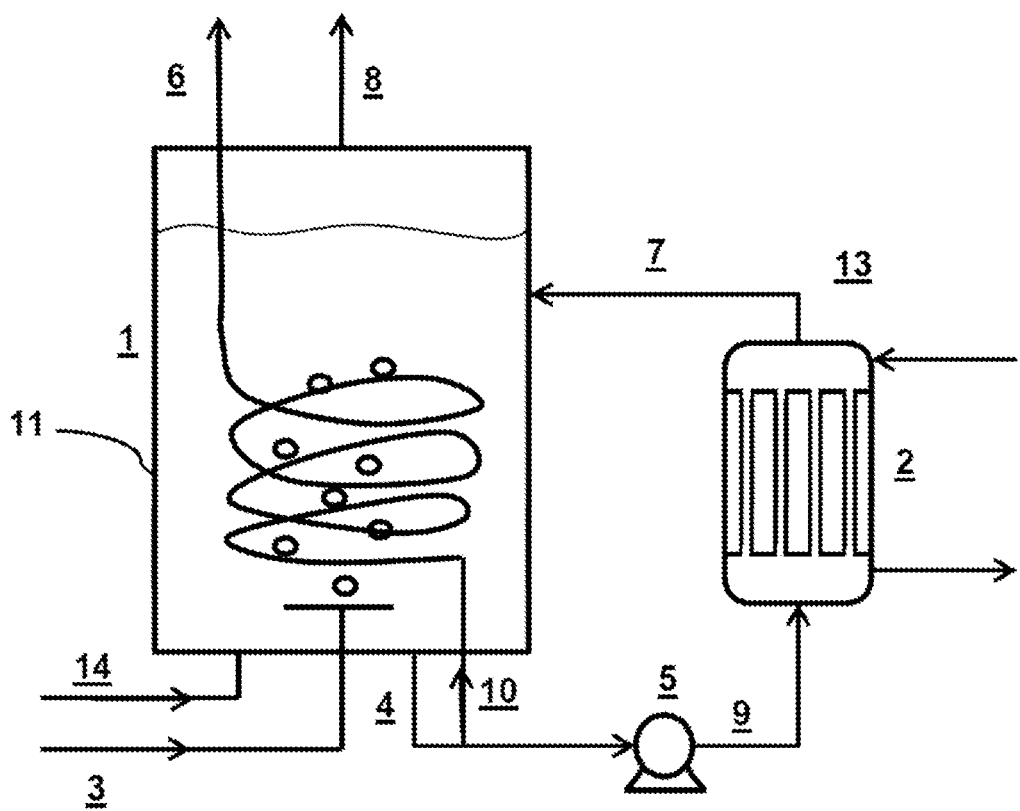
FIG. 4 illustrates another embodiment of the process according to the invention, in which the reactor of plug-flow type 11 is present within even the gas/liquid reactor 1.

Preferably, stage e) is carried out by the circulation of the said liquid fraction through a reactor of plug-flow type, located outside the gas/liquid reactor (cf. embodiment according to FIG. 3) or inside (cf. embodiment according to FIG. 4), and preferably outside.

According to a first embodiment, the plug-flow reactor comprises a heat exchanger (not represented in the figures), in which a cooling liquid 12 circulates (cf. FIG. 3).

In a second embodiment, the plug-flow reactor is immersed in the gas/liquid reactor. The two reactors thus constitute a heat exchanger in which the liquid phase of the gas/liquid reactor acts as cooling liquid (cf. FIG. 4).

The circulation of the liquid fraction can be carried out just as easily cocurrentwise as countercurrentwise to the cooling liquid circulating in the heat exchanger. Preferably, the circulation between the said liquid fraction and the said cooling liquid is carried out cocurrentwise, thus making it possible to regulate the temperature of the said liquid fraction and preferably to have a controlled temperature of the said liquid fraction flowing in the plug-flow reactor.

During the flowing of the liquid fraction in the reactor of plug-flow type, there is exchange of heat between the said fraction and the cooling liquid. Thus, the temperature of the liquid fraction is controlled, limiting the increase in temperature, making it possible for the oligomerization reaction to continue at the desired temperature and to thus obtain an increase in the conversion with a virtually unchanging selectivity.

The cooling liquid advantageously makes it possible to cool and thus to limit the increase in the temperature of the said fraction to between 1.0 and 11.0° C., preferably between 2.0 and 10.0° C., preferably between 3.0 and 9.0° C., with respect to the temperature at the inlet of the plug-flow reactor, which is also the temperature for oligomerization of the liquid phase in the gas/liquid reactor.

Advantageously, the limitation on the increase in the temperature makes it possible to continue the conversion of the olefins, while maintaining the selectivity of the said products. The limitation on the increase in temperature within the reactor of plug-flow type corresponds to the difference in temperature between the temperature of the liquid fraction at the inlet of the said reactor and the temperature of the liquid fraction at the outlet of the said reactor of plug-flow type. This difference in temperature of the said liquid fraction depends directly on the residence time of the said liquid fraction within the said reactor and thus on the flow rate within the said reactor. This difference in temperature of the said fraction also depends on the contact surface area between the said liquid fraction present in the reactor of plug-flow type and the cooling liquid or, according to another embodiment, between the said liquid fraction present in the reactor of plug-flow type and the liquid of the gas/liquid reactor. The contact surface area is between 20 and $10^6$ m$^2$, preferably between 50 and 200 000 m$^2$ and more preferably still between 30 and 50 000 m$^2$.

According to one embodiment, the temperature of the liquid fraction flowing in the plug-flow reactor is unchanging.

According to another embodiment, the temperature of the liquid fraction increases as it flows within the plug-flow reactor.

Stage f) of Recovery of the Reaction Effluent

The process according to the invention comprises a stage f) of recovery of a reaction effluent, at the outlet of the reactor of plug-flow type employed in stage e) of the said process. The reaction effluent comprises the desired products, such as linear olefins and more particularly linear α-olefins, the reactants of the reaction (the catalytic system and the olefin introduced) and optionally the solvent and/or the additive.

The catalytic system is advantageously deactivated continuously by any usual means known to a person skilled in the art and then the products resulting from the reaction, and also the solvent, are separated, for example by distillation. The residues of the catalytic system included in a heavy fraction can be incinerated. The olefin which has not been converted can be recycled. The fact of not injecting the olefin directly into the reactor of plug-flow type makes it possible to improve the conversion and to decrease the concentration of olefin all along the reactor. This results in a decrease in the costs for implementation of the process (recycling, separation, destruction).

The products resulting from the reaction are preferably linear α-olefins, such as linear olefins comprising from 4 to 12 carbon atoms, preferably from 4 to 8 carbon atoms. Preferably, the linear α-olefins are chosen from but-1-ene, hex-1-ene or oct-1-ene.

Figure 2A:
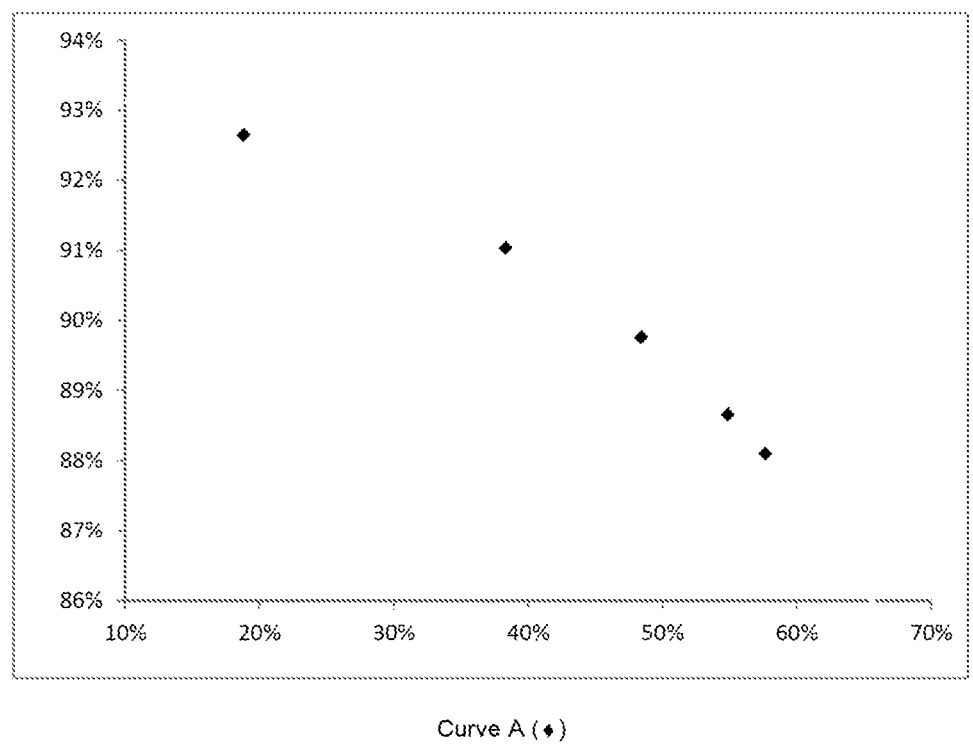
FIGS. 2A and 2B represent the selectivity as a function of the conversion, with the selectivity, expressed as percentage, on the axis of the ordinates and the conversion, also expressed as percentage, on the axis of the abscissae.
Figure 2B:
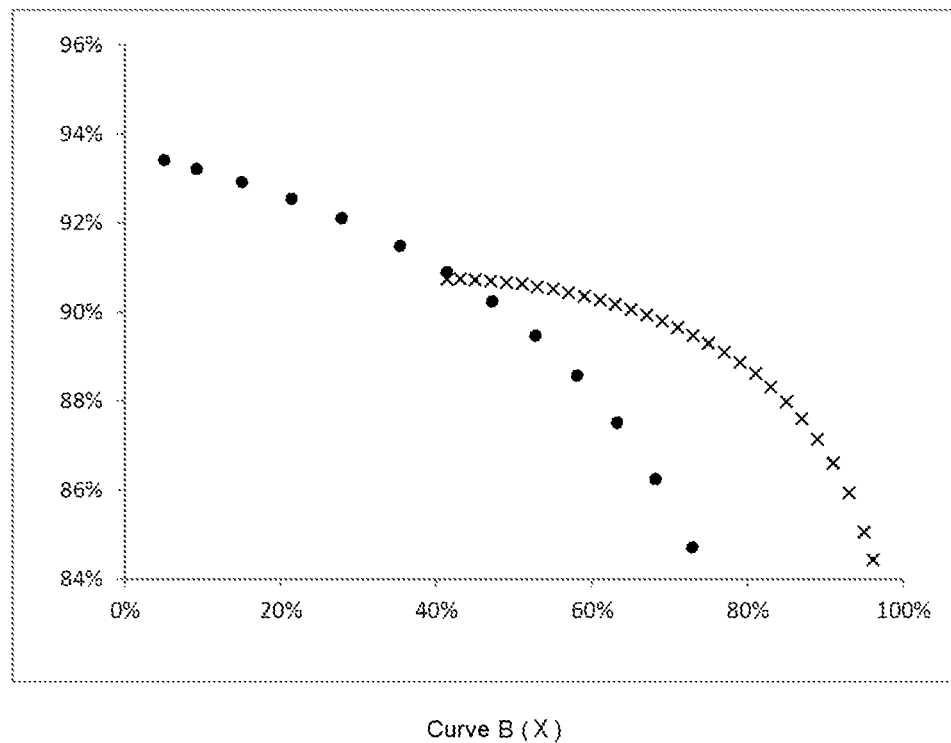

On referring to the curve of FIG. 2B (represented by crosses), it is noteworthy to observe that the process according to the invention makes it possible, under operating conditions equivalent to those of the prior art, to improve the conversion of olefins while retaining a good selectivity for desired products, i.e. for linear α-olefins. There exists an infinity of curves such as the curve of FIG. 2B represented by crosses, according to the point of selectivity chosen for improving the conversion. The profiles of these curves are substantially identical.

Oligomerization Reaction Device

Another subject-matter of the invention relates to the reaction device which makes possible the implementation of the process according to the invention; the said device comprises:

- a gas/liquid reactor 1, of elongated shape along the vertical axis, comprising a liquid phase and a gas phase located above the said liquid phase,
- a means for introduction of the olefin 3 into the gas/liquid reactor employing a means for injection of the olefin within the said liquid phase of the gas/liquid reactor,
- a means for introduction of the catalytic system 14 into the gas/liquid reactor,
- a recirculation loop 13 comprising withdrawal means in the gas/liquid reactor for the withdrawal and the dispatch of a fraction of withdrawn liquid to a heat exchanger capable of cooling the said liquid fraction, and means for introduction of the said cooled liquid, exiting from the heat exchanger, into the upper part of the gas/liquid reactor 1, a reactor of plug-flow type 11 comprising withdrawal means in the gas/liquid reactor for the withdrawal and the dispatch of a fraction of withdrawn liquid to the plug-flow reactor and means for recovery of a reaction effluent, at the outlet of the plug-flow reactor.

The residence time of the liquid fraction in the oligomerization reaction device is, on average, between 30 and 400 minutes, preferentially between 30 and 150 minutes, preferably between 40 and 130 minutes.

(i) A Gas/Liquid Reactor

According to the invention, any gas/liquid reactor known to a person skilled in the art and capable of carrying out the process according to the invention can be envisaged. Preferably, the gas/liquid reactor is of cylindrical shape and exhibits a height to width ratio (denoted H/D) between 1 and 8, preferably between 1 and 4.

Preferably, the gas/liquid reactor comprises a means for bleeding off the non-condensable gases.

Preferably, the gas/liquid reactor also comprises a pressure sensor which makes it possible to keep the pressure within the gas/liquid reactor constant. Preferably, the said pressure is kept constant by the introduction of additional olefin into the gas/liquid reactor.

Preferably, the gas/liquid reactor also comprises a liquid level sensor; the said level is kept constant by adjusting the flow rate of the effluent withdrawn in stage c). Preferably, the level sensor is located at the interphase between the liquid phase and the gas headspace.

(ii) A Means for Introduction of the Olefin

According to the invention, the gas/liquid reactor 1 comprises a means for introduction of the olefin located in the lower part of the said reactor, more particularly in the bottom of the gas/liquid reactor.

Preferably, the means for introduction of the olefin 3 is chosen from a pipe, a network of pipes, a multitubular distributor, a perforated plate or any other means known to a person skilled in the art.

In a specific embodiment, the means for introduction of the olefin is located in the recirculation loop 13.

Preferably, a gas distributor, which is a device which makes it possible to disperse the gas phase uniformly over the entire liquid section, is positioned at the end of the means for introduction 3 within the gas/liquid reactor 1. The said device comprises a network of perforated pipes, the diameter of the orifices of which is between 1 and 12 mm, preferably between 3 and 10 mm, in order to form ethylene bubbles in the liquid of millimetric size.

Preferably, the velocity of the olefin at the outlet of the orifices is between 1 and 30 m/s. Its superficial velocity (gas volumetric velocity divided by the section of the gas/liquid reactor) is between 0.5 and 10 cm/s and preferably between 1 and 8 cm/s.

(iii) A Means for Introduction of the Catalytic System

According to the invention, the gas/liquid reactor 1 comprises a means for introduction 14 of the catalytic system.

Preferably, the means for introduction of the catalytic system 14 is located over the lower part of the gas/liquid reactor and preferably in the bottom of the said reactor. According to a preferred alternative embodiment, the introduction of the catalytic system is carried out in the recirculation loop.

The means for introduction 14 of the catalytic system is chosen from any means known to a person skilled in the art and is preferably a pipe.

In the embodiment where the catalytic system is employed in the presence of a solvent or of a mixture of solvents, the said solvent is introduced by an introduction means located in the lower part of the gas/liquid reactor, preferably in the bottom of the gas/liquid reactor, or also in the recirculation loop.

(iv) A Recirculation Loop

According to the invention, the homogeneity of the liquid phase, and also the regulation of the temperature within the gas/liquid reactor 1, are achieved by the use of a recirculation loop 13 comprising a withdrawal means, a heat exchanger and a means for reintroduction of the cooled liquid fraction.

The withdrawal means is located over the lower part of the gas/liquid reactor, preferably under the level of introduction of the olefin and preferably in the bottom of the reactor. A first fraction of the withdrawn liquid is sent to a heat exchanger, making possible the cooling of the said liquid. The said cooled liquid is subsequently reintroduced into the gas headspace at the top of the gas/liquid reactor 1.

The recirculation loop can advantageously be implemented by any necessary means known to a person skilled in the art, such as a pump for the withdrawal of the liquid fraction, a means capable of regulating the flow rate of the withdrawn liquid fraction, or also a pipe for bleeding off at least a portion of the liquid fraction.

Preferably, the means for withdrawal of the liquid fraction from the gas/liquid reactor is a pipe.

The heat exchanger(s) capable of cooling the liquid fraction is (are) chosen from any means known to a person skilled in the art.

The recirculation loop makes possible good homogenization of the concentrations and makes it possible to control the temperature in the liquid fraction within the gas/liquid reactor.

According to the invention, the liquid fraction cooled in the recirculation loop 13 is reintroduced into the upper part of the gas/liquid reactor, preferably at the top of the said reactor, in a preferred way into the gas phase, by any means known to a person skilled in the art.

(v) A Reactor of Plug-Flow Type

According to the invention, a second fraction of the withdrawn liquid is sent to a reactor of plug-flow type 11. The reactor of plug-flow type can be located outside the gas/liquid reactor or inside the latter; preferably, the reactor of plug-flow type is located outside the gas/liquid reactor.

Preferably, the plug-flow reactor also comprises a pressure sensor which makes it possible to display and to keep the pressure within the reactor constant. Preferably, the said pressure is kept constant by control means which make it possible to manage the flow rate of liquid entering the plug-flow reactor and the flow rate of effluent exiting from the plug-flow reactor. The said control means can be any means known to a person skilled in the art, such as valves.

In a preferred embodiment, the reactor of plug-flow type comprises a heat exchanger suitable for the cooling of the said liquid fraction. The heat exchanger is cocurrent or countercurrent; preferably, the heat exchanger is cocurrent.

In another embodiment, the reactor of plug-flow type is located inside the gas/liquid reactor, the two reactors together constituting a heat exchanger.

The reaction effluent is recovered at the outlet of the reactor of plug-flow type.

One advantage of the present invention is thus that of making it possible to achieve selectivities for linear olefins and preferably for linear α-olefins which are superior to those achieved with a device according to the prior art comprising only a single gas/liquid reactor, this being obtained while retaining a high level of conversion into linear olefins and preferably into linear α-olefins.

EXAMPLES

The examples below illustrate the invention without limiting the scope thereof.

Example 1 (Comparative)

Example 1 illustrates the reference case corresponding to the curve of FIG. 2A, in which the oligomerization process employs a gas/liquid reactor according to the prior art.

A mixture of chromium tris(2-ethylhexanoate) (denoted Cr(2-EH)3), of bis(2-(tert-butyl)-6-phenylphenoxy)magnesium and of dibutyl ether (in a 1/1/2 molar ratio) at 0.3 mol/l in a cyclohexane/heptane mixture is prepared in accordance with the protocol described in Patent Application FR 3 019 064.

Implementation of the Process for the Oligomerization of Ethylene According to the Prior Art, at a Pressure of 5.3 MPa and at a Temperature of 135° C., Comprising the Following Stages:

the chromium-based catalytic system composed of Cr(2-EH)3, of bis(2-(tert-butyl)-6-phenylphenoxy)magnesium, of dibutyl ether and of triethylaluminium (Cr/Mg/DBE/Al molar ratio 1/1/2/2.5) is introduced, in the presence of a solvent which is cyclohexane, so as to obtain a content of 5 ppm of chromium, into the liquid phase of a 146 m$^3$ gas/liquid reactor comprising a liquid phase and a gas phase;

the said catalytic system is brought into contact with ethylene by introducing the gaseous ethylene into the lower part of the said gas/liquid reactor; the residence time in the gas/liquid reactor is 16 minutes;

the reaction effluent is recovered.

The volumetric productivity of this reactor is 214 kg of α-olefin produced per hour and per m$^3$ of reaction volume.

The performance qualities of this reactor make it possible to convert 50.90% of the injected ethylene and to achieve a selectivity of 89.70% for the desired α-olefin, for a content by weight of solvent of 3.2. The said content of solvent is calculated as the ratio by weight of the flow rate of injected solvent to the flow rate of injected gaseous ethylene.

Example 2 (According to the Invention)

Example 2 illustrates the case corresponding to the curve of FIG. 2B (represented by crosses), in which the oligomerization process employs a sequence of a gas/liquid reactor and of a reactor of plug-flow type.

The catalytic composition used is identical to that used in Example 1.

Implementation of the Process for the Oligomerization of Ethylene According to the Invention, at a Pressure of 5.3 MPa and at a Temperature of 135° C., Comprising the Following Stages:

a) the chromium-based catalytic oligomerization system is introduced at a content of 5 ppm of chromium, in the presence of a solvent which is cyclohexane, into a 91 m$^3$ gas/liquid reactor comprising a liquid phase and a gas phase; the residence time in this first reactor is 12 minutes;

b) the said catalytic system is brought into contact with ethylene by introducing the ethylene into the lower part of the said gas/liquid reactor;

c) reaction liquid is withdrawn in the lower part of the said gas/liquid reactor;

d) a first fraction of the liquid withdrawn in stage c) is sent to a heat exchanger in order to obtain a cooled liquid fraction and the said cooled liquid fraction is reintroduced into the upper part of the said gas/liquid reactor;

e) a second fraction of the liquid withdrawn in stage c) is sent to a 73 m$^3$ reactor of plug-flow type at a flow rate of between 1 and 500 t/h; the residence time of the said liquid fraction in the plug-flow reactor is 9 minutes, being between 1 and 30 minutes;

f) a reaction effluent is recovered at the outlet of the reactor of plug-flow type.

The volumetric productivity of this reactor is 190 kg of α-olefin produced per hour and per m$^3$ of reaction volume.

The performance qualities of this reactor make it possible to convert 69.00% of the injected ethylene and to achieve a selectivity of 89.70% for the desired α-olefin, for a content by weight of solvent of 3.9. The said content of solvent is calculated as the ratio by weight of the flow rate of injected solvent to the flow rate of injected gaseous ethylene.

For one and the same selectivity for desired α-olefin as in the preceding example, the reactor according to the invention makes it possible to significantly improve the conversion of the ethylene: more than 18% extra conversion.

The invention claimed is:

1. Device comprising:
    a gas/liquid reactor (1), of elongated shape along the vertical axis, comprising a liquid phase part and a gas phase upper part located above the liquid phase part,
    a means for introduction of an olefin (3) into the gas/liquid reactor employing a means for injection of the olefin within the liquid phase of the gas/liquid reactor,
    a means for introduction of a catalytic system (14) into the gas/liquid reactor,
    a recirculation loop (13) comprising withdrawal means from the gas/liquid reactor for the withdrawal and the dispatch of a withdrawn liquid fraction from the liquid phase part to a heat exchanger capable of cooling the liquid fraction, and means for introduction of the resulting cooled liquid fraction, exiting from the heat exchanger, into the upper part of the gas/liquid reactor (1),
    withdrawal means from the gas/liquid reactor for the withdrawal and the dispatch of a fraction of withdrawn liquid to a plug-flow reactor,
    a plug-flow reactor (11) in which the fraction of withdrawn liquid flows; wherein the plug-flow reactor is located outside the gas/liquid reactor, the plug-flow reactor comprises a heat exchanger wherein cooling liquid flows and the cooling liquid flow is cocurrentwise with the fraction of withdrawn liquid flow in the plug-flow reactor, and
    means for recovery of a reaction effluent from an outlet of the plug-flow reactor.

2. Olefin oligomerization process employing the device according to claim 1, at a pressure between 1.0 and 10.0 MPa and at a temperature between 0° C. and 200° C., comprising the following stages:
    a) introducing a catalytic oligomerization system comprising at least one metal precursor and at least one activating agent into the gas/liquid reactor (1) comprising the liquid phase part and the gas phase upper part;
    b) bringing the catalytic oligomerization system into contact with the olefin by introducing the olefin (3) into the gas/liquid reactor (1) and forming a resulting reaction liquid;

c) withdrawing the reaction liquid from the liquid part of the gas/liquid reactor;
d) sending a first fraction of the liquid (9) withdrawn in stage c) to a heat exchanger (2), obtaining a cooled liquid fraction from the heat exchanger and then introducing the cooled liquid fraction into the upper part of the gas/liquid reactor;
e) sending a second fraction of the liquid (10) withdrawn in stage c) to the plug-flow reactor (11), the residence time of the second liquid fraction in the plug-flow reactor being between 1 and 30 minutes, the increase in temperature of the second liquid fraction in the plug-flow reactor being limited to between 1.0 and 11.0° C.; wherein the plug-flow reactor is located outside the gas/liquid reactor, the plug-flow reactor comprises a heat exchanger wherein cooling liquid flows and the cooling liquid flow is cocurrentwise with the second liquid fraction flow in the plug-flow reactor;
f) recovering a reaction effluent (6) at the outlet of the plug-flow reactor.

3. Oligomerization process according to claim 2, in which the metal precursor used in the catalytic system is chosen from compounds based on nickel, on titanium or on chromium.

4. Oligomerization process according to claim 3, in which the concentration of nickel, of titanium or of chromium is between 0.01 and 300.0 ppm by weight of atomic metal, with respect to the reaction mass.

5. Oligomerization process according to claim 2, in which the catalytic system additionally comprises one or more activating agents chosen from aluminium-based compounds, methylaluminium dichloride (MeAlCl$_2$), dichloroethylaluminium (EtAlCl$_2$), ethylaluminium sesquichloride (Et$_3$Al$_2$Cl$_3$), chlorodiethylaluminium (Et$_2$AlCl), chlorodiisobutylaluminium (i-Bu$_2$AlCl), triethylaluminium (AlEt$_3$), tripropylaluminium (Al(n-Pr)$_3$), triisobutylaluminium (Al(i-Bu)$_3$), diethylethoxyaluminium (Et$_2$AlOEt), methylaluminoxane (MAO), ethylaluminoxane and modified methylaluminoxanes (MMAO).

6. Oligomerization process according to claim 2, in which the catalytic system comprises one or more additives.

7. Oligomerization process according to claim 2, in which the olefin is ethylene.

8. Process according to claim 2, in which the reaction effluent comprises linear olefins comprising between 4 and 12 carbon atoms.

9. Process according to claim 8, in which the linear olefins obtained comprise linear α-olefins chosen from but-1-ene, hex-1-ene or oct-1-ene.

10. Oligomerization process according to claim 2, in which the catalytic system comprises one or more solvents.

11. Oligomerization process according to claim 3, in which the concentration of nickel, of titanium or of chromium is between 0.02 and 100.0 ppm by weight of atomic metal, with respect to the reaction mass.

12. Oligomerization process according to claim 3, in which the concentration of nickel, of titanium or of chromium is between 0.03 and 50.0 ppm by weight of atomic metal, with respect to the reaction mass.

13. Oligomerization process according to claim 3, in which the concentration of nickel, of titanium or of chromium is between 0.5 and 20.0 ppm by weight of atomic metal, with respect to the reaction mass.

14. Oligomerization process according to claim 3, in which the concentration of nickel, of titanium or of chromium is between 2.0 and 50.0 ppm by weight of atomic metal, with respect to the reaction mass.

15. Olefin oligomerization process employing the device according to claim 1, at a pressure between 1.0 and 10.0 MPa and at a temperature between 0° C. and 200° C., comprising the following stages:
a) introducing a catalytic oligomerization system comprising at least one metal precursor and at least one activating agent into the gas/liquid reactor (1) comprising the liquid phase part and the gas phase upper part;
b) bringing the catalytic oligomerization system into contact with the olefin by introducing the olefin (3) into the gas/liquid reactor (1) and forming a resulting reaction liquid;
c) withdrawing the reaction liquid from the liquid part of the gas/liquid reactor;
d) sending a first fraction of the liquid (9) withdrawn in stage c) to a heat exchanger (2), obtaining a cooled liquid fraction from the heat exchanger and then introducing the cooled liquid fraction into the upper part of the gas/liquid reactor;
e) sending a second fraction of the liquid (10) withdrawn in stage c) to the plug-flow reactor (11), the residence time of the second liquid fraction in the plug-flow reactor being between 1 and 30 minutes, the increase in temperature of the second liquid fraction in the plug-flow reactor being limited to between 1.0 and 11.0° C.; wherein the plug-flow reactor is located immersed in the gas/liquid reactor, the plug-flow reactor immersed in the gas/liquid reactor together being a heat exchanger wherein the liquid phase of the gas/liquid reactor acts as cooling liquid and the cooling liquid flow is cocurrentwise with the second liquid fraction flow in the plug-flow reactor;
f) recovering a reaction effluent (6) at the outlet of the plug-flow reactor.

16. Oligomerization process according to claim 15, in which the metal precursor used in the catalytic system is chosen from compounds based on nickel, on titanium or on chromium.

17. Oligomerization process according to claim 16, in which the concentration of nickel, of titanium or of chromium is between 0.01 and 300.0 ppm by weight of atomic metal, with respect to the reaction mass.

18. Oligomerization process according to claim 15, in which the catalytic system additionally comprises one or more activating agents chosen from aluminium-based compounds, methylaluminium dichloride (MeAlCl$_2$), dichloroethylaluminium (EtAlCl$_2$), ethylaluminium sesquichloride (Et$_3$Al$_2$Cl$_3$), chlorodiethylaluminium (Et$_2$AlCl), chlorodiisobutylaluminium (i-Bu$_2$AlCl), triethylaluminium (AlEt$_3$), tripropylaluminium (Al(n-Pr)$_3$), triisobutylaluminium (Al(i-Bu)$_3$), diethylethoxyaluminium (Et$_2$AlOEt), methylaluminoxane (MAO), ethylaluminoxane and modified methylaluminoxanes (MMAO).

19. Oligomerization process according to claim 15, in which the catalytic system comprises one or more additives.

20. Oligomerization process according to claim 15, in which the olefin is ethylene.

21. Process according to claim 15, in which the reaction effluent comprises linear olefins comprising between 4 and 12 carbon atoms.

22. Process according to claim 21, in which the linear olefins obtained comprise linear α-olefins chosen from but-1-ene, hex-1-ene or oct-1-ene.

23. Oligomerization process according to claim 15, in which the catalytic system comprises one or more solvents.

24. Device comprising:
- a gas/liquid reactor (1), of elongated shape along the vertical axis, comprising a liquid phase part and a gas phase upper part located above the liquid phase part,
- a means for introduction of an olefin (3) into the gas/liquid reactor employing a means for injection of the olefin within the liquid phase of the gas/liquid reactor,
- a means for introduction of a catalytic system (14) into the gas/liquid reactor,
- a recirculation loop (13) comprising withdrawal means from the gas/liquid reactor for the withdrawal and the dispatch of a withdrawn liquid fraction from the liquid phase part to a heat exchanger capable of cooling the liquid fraction, and means for introduction of the resulting cooled liquid fraction, exiting from the heat exchanger, into the upper part of the gas/liquid reactor (1),
- withdrawal means from the gas/liquid reactor for the withdrawal and the dispatch of a fraction of withdrawn liquid to a plug-flow reactor,
- a plug-flow reactor (11) in which the fraction of withdrawn liquid flows; wherein the plug-flow reactor is located immersed in the gas/liquid reactor, the plug-flow reactor immersed in the gas/liquid reactor together being a heat exchanger wherein the liquid phase of the gas/liquid reactor acts as cooling liquid, and wherein said liquid phase of the gas/liquid reactor acting as cooling liquid flows cocurrentwise with the fraction of withdrawn liquid flow in the plug-flow reactor, and
- means for recovery of a reaction effluent from an outlet of the plug-flow reactor.

\* \* \* \* \*